United States Patent [19]
Davis et al.

[11] Patent Number: 6,030,827
[45] Date of Patent: Feb. 29, 2000

[54] MICROFABRICATED APERTURE-BASED SENSOR

[75] Inventors: Graham Davis, Princeton; Chao Lin, Monmouth Junction, both of N.J.; Imants R. Lauks, Rockcliffe Park; Raymond J. Pierce, Ottawa, both of Canada

[73] Assignee: i-Stat Corporation, East Windsor, N.J.

[21] Appl. No.: 09/012,579

[22] Filed: Jan. 23, 1998

[51] Int. Cl.[7] ................................................. C12M 1/40
[52] U.S. Cl. ................................ 435/287.1; 435/287.8; 435/287.9; 435/288.7; 435/817; 204/403; 204/415; 422/82.01; 422/82.06
[58] Field of Search .............................. 435/28.1, 287.2, 435/287.9, 288.7, 817; 204/403, 415; 422/82.01, 82.02, 82.06, 82.07

[56] References Cited

U.S. PATENT DOCUMENTS

| | | |
|---|---|---|
| 4,484,987 | 11/1984 | Gough . |
| 4,650,547 | 3/1987 | Gough . |
| 4,654,197 | 3/1987 | Lilja et al. ................................ 422/56 |
| 4,682,602 | 7/1987 | Prohaska . |
| 4,759,828 | 7/1988 | Young et al. . |
| 4,832,797 | 5/1989 | Vadgama et al. . |
| 4,886,740 | 12/1989 | Vadgama . |
| 4,890,620 | 1/1990 | Gough . |
| 4,897,173 | 1/1990 | Nankai et al. . |
| 4,933,048 | 6/1990 | Lauks ..................................... 205/789 |
| 5,112,455 | 5/1992 | Cozzette et al. . |
| 5,185,256 | 2/1993 | Nankai et al. . |
| 5,200,051 | 4/1993 | Cozzette et al. . |
| 5,262,305 | 11/1993 | Heller et al. . |
| 5,326,449 | 7/1994 | Cunningham . |
| 5,327,223 | 7/1994 | Korth . |
| 5,352,348 | 10/1994 | Young et al. . |
| 5,356,786 | 10/1994 | Heller et al. . |
| 5,437,973 | 8/1995 | Vadgama et al. . |
| 5,466,575 | 11/1995 | Cozzette et al. ............................. 435/6 |
| 5,514,253 | 5/1996 | Davis et al. . |
| 5,696,314 | 12/1997 | McCaffrey et al. ................... 73/53.01 |
| 5,719,033 | 2/1998 | Ackley et al. ........................... 435/7.92 |
| 5,804,048 | 9/1998 | Wong et al. ............................. 204/403 |

OTHER PUBLICATIONS

U. Fischer et al., "Implantable Glucose Sensors" (1982) *Trans Am Soc Inter Organs* vol. 28, pp. 245–248.

Gough, et al., "Two–Dimensional Enzyme Electrode Sensor for Glucose" *Anal. Chem.* 1985, vol. 57, pp. 2351–2357.

Jean–Michel Saveant, "Premeation through polymer coatings on electrodes Membrane versus pinhole permeation" *J. Electroanal. Chem.,* (1991), vol. 302, pp. 91–101.

Blonder, et al. "Glucose enzyme electrode with percutaneous interface which operates independently of dissolved oxygen." *Anal. Chem.* (1996) 68 (18) pp. 3151–3157.

Madaras, et al., "Microfabricated amperometric creatine and creatinine biosensors." *Analytica Chimica Acta.* vol. 319 (1996) pp. 335–345.

J. Schneider, et al., "Hydrogel Matrix for three enzyme entrapment in creatine/creatinine amperometric biosensing." *Analytica Chimica Acta,* vol. 325 (1996) pp. 161–167.

Hitoshi Yamato, et al., "A Polypyrrole/Three–Enzyme Electrode for Creatinine Detection." *Anal. Chem.* (1995) vol. 67, pp. 2776–2780.

Tsuchida, et al., "Multi–Enyme Membrane Electrodes for Determination of Creatinine and Creatine in Serum." *Clin. Chem.* (1983) vol. 29/1, pp. 51–55.

Abel, et al."Experience with an implantable glucose sensor as a prerequisite of an artificial beta cell." *Biomed. Biochim. Acta.* 43 (1984) vol. 5, pp. 577–584.

*Primary Examiner*—William H. Beisner
*Attorney, Agent, or Firm*—Gilberto M. Villacorta; Pepper Hamilton LLP

[57] ABSTRACT

A chemical sensor includes an enzyme layer, a diffusion layer and an analyte barrier layer positioned over the diffusion layer. Apertures are formed by microfabrication in the analyte barrier layer to allow controlled analyte flux to the diffusion layer.

49 Claims, 12 Drawing Sheets

MICROFABRICATED APERTURE-BASED SENSOR

TECHNICAL FIELD

This invention relates to the detection of molecules (analytes) present in fluids such as blood. More particularly, the invention relates to the detection of organic molecules in vitro using an amperometric catalytic-based sensor. In specific embodiments of the invention, sensors formed by microfabrication processes and having novel device designs can be used to perform assays of various molecules, including glucose, lactate, cholesterol, pyruvate, sarcosine, bilirubin, and creatinine, present in blood and other bodily fluids.

BACKGROUND OF THE INVENTION

Assaying bodily fluids such as blood for levels of various organic molecules is useful in the treatment of diseased states. For example, diabetes mellitus is a disease characterized by poor regulation of blood glucose levels. The traditional treatments for mild forms of this disease, including adult onset diabetes, have included diet and exercise. More severe forms, however, require administration of insulin. One of the drawbacks of administering insulin is the possibility of insulin shock, caused by rapid decrease in blood glucose levels (glucose imbalance) due to unintended over medication. Insulin shock is, however, only the most severe manifestation of glucose imbalance. The consequences of chronic glucose imbalance (both over and under medication) are well documented and include damage to blood vessels and various body organs. Blindness is common, as is the loss of circulation in the extremities.

Accurate measurement of blood glucose levels would enable the patient to modulate insulin dosage and avoid the effects of chronic glucose imbalance. One example of a prior art attempt at glucose measurement is a glucose sensor as disclosed in U.S. Pat. No. 3,542,662. In this device, an enzyme-containing membrane is disposed between a fluid being assayed and a first oxygen sensor electrode. A similar membrane not containing enzyme is disposed between the fluid and a second reference oxygen sensor electrode. A certain portion of the oxygen diffusing through the enzyme-containing membrane is consumed by equimolar reaction with glucose catalyzed by the enzyme and is therefore unavailable for detection by the first oxygen sensor electrode. The second, reference oxygen sensor electrode, in which the membrane does not include enzyme, determines the concentration of oxygen that would have been detected had not the enzyme-promoted reaction occurred. The difference in oxygen detected by the two electrodes is indicative of the glucose concentration.

A problem with this device is that the levels of oxygen and glucose in the blood are less than stoichiometric. In particular, the amount of oxygen is less than that needed to convert all the glucose. Thus the sensor can become oxygen limited and not respond accurately at high glucose concentrations.

In order to bring the levels of glucose and oxygen to stoichiometric balance and thus create a device that gives accurate results over the complete range of glucose concentrations found in blood, it has been proposed to design sensors that reduce the amount of glucose reaching the enzyme layer relative to oxygen. This could be accomplished in theory by providing a membrane layer which is significantly more permeable to oxygen than glucose. U.S. Pat. No. 4,650,547, described more fully hereinbelow, provides a general description of this concept.

Implementing this approach has heretofore been difficult, however, due to the prior art's inability to precisely and reproducibly control the permeability of the membrane. Without such precise control, the glucose flux reaching the enzyme layer may not be sufficiently attenuated. Problems can also arise due to the presence of interferant molecules, e.g. ascorbate and urate. The determination of creatinine levels, which is used to measure renal function, is an example of an analyte that requires removal of these interferants.

U.S. Pat. No. 4,933,048 relates to water permeable, ion impermeable membranes microfabricated over a hydrogel layer leaving an opening for ion exchange. FIG. 2 of the '048 patent illustrates a structure where the opening is formed by having the hydrogel layer extend beyond the ion impermeable layer. Alternatively, the ion impermeable layer can cover the entire hydrogel layer with holes formed beyond the perimeter of the underlying electrode (column 7, line 1). Holes can be formed by laser perforation or other methods. The aperture is formed at a distance from the electrode and the function of the small opening is to provide a low impedance electrolytic junction.

Glucose sensors using non-microfabricated or "macro" electrodes are known. See, for example, Fischer, U. and Abel, P., Transactions of the *American Society of Artificial Internal Organs* 1982, 28, 245–248 (Fischer et al.); Rehwald, W., *Pflugers Archiv* 1984, 400, 348–402; U.S. Pat. Nos. 4,484,987; 4,515,584; and 4,679,562; and UK Patent Application 2,194,843. However, no aspect of thin-film processing is described in these documents.

Fischer et al. discloses a non-microfabricated glucose sensor with a Teflon® membrane which is mechanically perforated. Glucose can only enter through the perforation whereas oxygen can pass through the Teflon®, thus adjusting the stoichiometry in the enzyme layer and linearizing the response. There is no teaching of optimizing or controlling the dimensions of the perforation. The Fischer et al. document is also silent on the use of microfabrication. East German patent DD 282527 appears to correspond to this publication but does not name Fischer as an inventor.

U.S. Pat. No. 4,484,987 relates to a linearized glucose sensor based on the concept of providing a layer with hydrophobic regions in a hydrophilic matrix where glucose can permeate the latter but not the former, and oxygen can permeate both regions (see description of FIG. 1 thereof. In an alternative embodiment, shown in FIG. 4, a hydrophobic layer includes spaced small openings through which glucose molecules can pass. However, the '987 patent provides no teaching of how the dimensions or location of the openings are controlled and is silent on microfabrication.

U.S. Pat. No. 4,650,547 discloses a glucose sensor where a hydrophobic gas permeable membrane is placed over a hydrophilic enzyme-containing layer, where only the perimeter or peripheral edge thickness surface of the hydrophilic layer is exposed to the sample (FIG. 5). Glucose can only enter the hydrophilic layer at the perimeter and diffuse parallel to the plane of the layer, whereas oxygen can be supplied across the entire surface of the hydrophobic layer (column 6, line 3).

Anal Chem 57, 2351, 1985 provides teaching for making a related cylindrical device where the gap between a platinum wire electrode and a gas permeable cylindrical coating is filled with an enzyme gel. There is no teaching, however, of microfabrication. U.S. Pat. No. 4,890,620 relates to a similar structure and method based on a differential measurement with a pair of sensors. An implantable version is disclosed in U.S. Pat. No. 4,703,756.

Regarding lactate and creatinine, there is comparatively little sensor literature. In Clin. Chem. 29, 51, 1983, there is proposed an amperometric creatinine sensor using three enzymes coupled to the production of hydrogen peroxide. This document also includes a differential measurement where one sensor measures creatine and the other measures creatine plus creatinine. The sensors are made using a cellulose acetate—glutaraldehyde method. Anal Chem 67, 2776, 1995 teaches electropolymerization to immobilize the creatinine enzymes onto an electrode. A poly(carbamoyl) sulphonate hydrogel is used in Anal Chim Acta 325, 161, 1996. None of the above documents teaches the use of microfabrication. Microdispensing to establish enzyme gel layers onto electrodes made by microfabrication is, however, disclosed in Anal Chim Acta 319, 335, 1996.

Despite the recent and significant advances in analyte sensors exemplified by U.S. Pat. Nos. 5,200,052 and 5,096,669, there remains a need in the art for improved microfabrication techniques and greater control of analyte flux. There is further a need in the art for reducing or eliminating the effect of interferant molecules on sensor measurement.

The measurement of glucose with a microfabricated sensor, described in U.S. Pat. No. 5,200,051, assigned to i-STAT Corporation, uses a thin contiguous analyte attenuation (AA) layer made from a silicone copolymer to cover an enzyme layer. It provides a membrane that is freely permeable to oxygen but is poorly permeable to glucose. This enables a linear response over the full range of glucose concentrations found in blood. As the '051 patent makes clear, oxygen is required in stoichiometric amounts to sustain the enzymatic reaction, despite the low levels generally present in blood. Using this membrane achieves this goal. The '051 patent includes a discussion of the general properties of a microfabricated analyte attenuation layer at column 12, beginning at line 57, with a more detailed description beginning at column 38, line 19. The etch process for the AA layer is discussed beginning at column 58, line 5. Structures with open perimeters for measuring glucose are illustrated in FIGS. 7A & 8A of the '051 patent, however, glucose transport occurs through a polysiloxane copolymer layer.

Wholly microfabricated sensors, that is, sensors which are uniformly mass-produced by thin-film techniques and micro-manufacturing methods, had not demonstrated utility in a clinical setting prior to the '051 patent. The '051 patent showed that the degree of complexity involved with the mass production of commercially viable biosensors was much more formidable than those persons of ordinary skill in the art once perceived. Of major concern was the compatibility of inherently harsh physical and chemical processes associated with the then existing commercial microfabrication manufacturing methods.

An article by Eleccion (Eleccion, M. Electronics 1986, Jun. 2, 26–30) describes the then current state of the art with regard to microsensors and makes brief references to active areas of research including the detection of specific ions, gases, and biological materials. Progress in the area of field effect transistors (FETs) is noted and problems and limitations with present manufacturing methods are discussed.

It is also important to note that in current clinical settings medical practitioners commonly request analyses of one or more components of a complex biological fluid such as whole blood. Currently, such analyses require a certain amount of processing of whole blood, such as filtration and centrifugation, to avoid contamination of the instruments or to simplify subsequent measurements. Frequently, blood samples are sent to a remote central laboratory where the analyses are performed. Patients and physicians are thus deprived of valuable information, which, in most cases, is not available for hours, sometimes days. Clearly, substantial advantages could be envisaged if analyses on undiluted samples could be carried out and if instruments or sensors were available perform real-time measurements. This can now be achieved using the point-of-care blood analysis system described in U.S. Pat. No. 5,096,669 (assigned to i-STAT Corporation).

Despite the recent and significant advances in chemical sensor technology as exemplified by U.S. Pat. Nos. 5,200,051 and 5,096,669, there remains a need in the art for improved microfabrication techniques and greater control of analyte flux. There is further a need in the art for reducing or eliminating the effect of interferant molecules on sensor measurement.

Disclosure of the Invention

It is accordingly an aspect of the invention to provide a chemical sensor capable of precise control of analyte diffusion rates or fluxes.

It is another aspect of the invention to provide a chemical sensor having a layer with one or more apertures for diffusional flux rate control and for controlling the stoichiometric ratio of co-reactant and analyte entering an enzyme layer.

It is another aspect of the invention to provide a sensor where the output characteristics thereof are not limited by the co-reactant concentration in a sample, and where the response of the sensor is essentially linear over the entire range of analyte concentrations commonly found in the sample.

It is another aspect of the invention to provide a chemical sensor that is single use and storable in a dry state, but which undergoes rapid wet-up on contacting a calibrant fluid.

It is yet another aspect of the invention to provide a chemical sensor that can be manufactured with a high degree of consistency from device to device in terms of both physical dimensions and output characteristics.

Yet another aspect of the invention is to provide a chemical sensor having a microfabricated diffusion layer or barrier of controlled geometry and character, that is permeable to a selected analyte molecule, and is interposed between a microfabricated aperture and a layer containing a catalyst (optionally an enzyme) that can interact with the analyte molecule.

It is yet another aspect of the invention to provide a chemical sensor with a layer that specifically screens out interferant species before they reach the enzyme layer.

Another aspect of the invention is to provide a chemical sensor that is single use and can be incorporated into a disposable cartridge for testing blood samples at a bedside and remote locations.

It is yet another aspect of the invention to provide a chemical sensor incorporating electrochemical optical and other sensing technologies that are amenable to substantially planar fabrication, for example, an acoustic wave sensor.

It is yet another aspect of the invention to provide methods for manufacturing the above-described chemical sensor.

These aspects, and others set forth more fully hereinbelow, are achieved by a microfabricated device for detecting an analyte molecule in a liquid sample which also contains a co-reactant, e.g. oxygen, which comprises: a transducing element; a first layer having a first side contacting the surface of said transducing element, the first layer comprising a support matrix containing at least one enzyme capable of catalyzing the conversion of said analyte and co-reactant into a reaction product detectable by the transducing element; a second layer in contact with the first layer, the second layer permitting transport of the analyte molecule and co-reactant; and a third layer covering the first and second layer, the third layer being permeable to co-reactant but substantially impermeable to the analyte molecule and containing at least one microfabricated aperture extending there through, which permits controlled transport of the analyte to the first layer.

BRIEF DESCRIPTION OF THE DRAWINGS

For a full understanding of the invention, the following detailed description should be read in conjunction with the drawings, wherein.

DETAILED DESCRIPTION OF THE PREFERRED EMBODIMENTS

Figure 1:
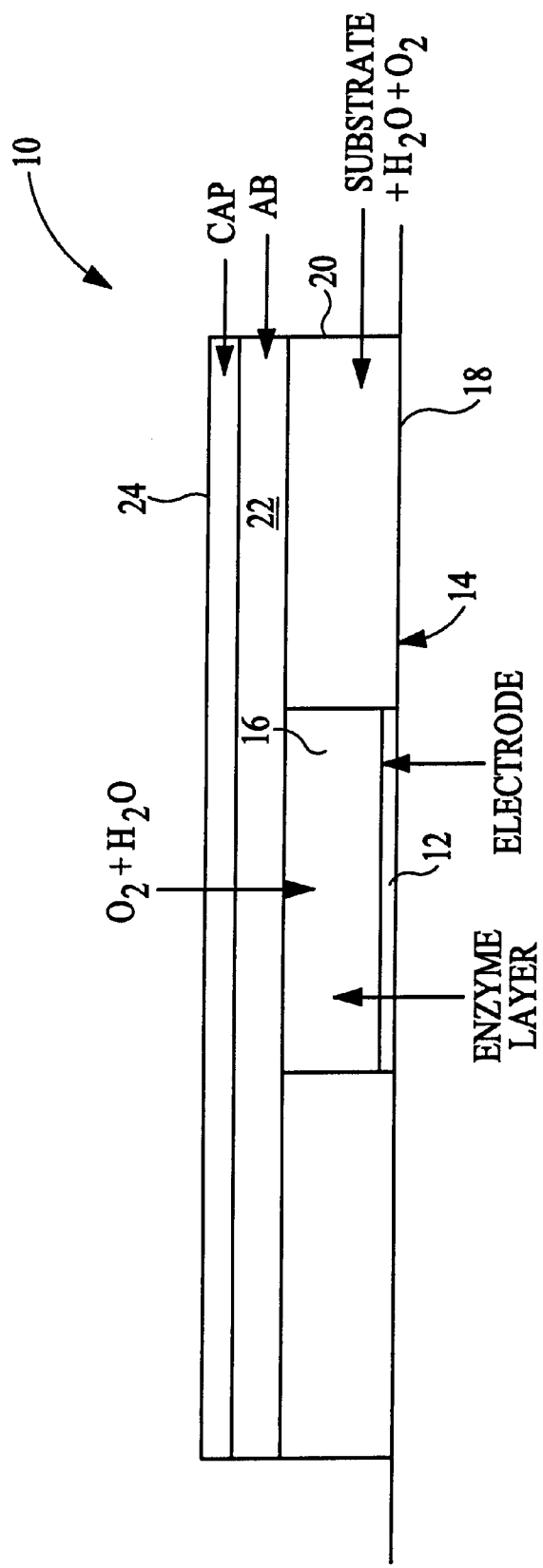
FIG. 1 is a schematic of one embodiment of the invention, illustrating a structure where the substrate (analyte molecule) can only enter the enzyme layer by passing through an edge-plane diffusion layer, whereas oxygen (co-reactant) passes in through a gas permeable layer.

The present invention relates to wholly microfabricated chemical sensors useful in measuring constituents (analytes) in various fluids. While the bulk of following detailed description concerns the use of chemical sensors to measure analytes found in biological fluids such as blood, it is to be understood that the invention encompasses use of the sensors in non-biological applications as well. Likewise, the term "analyte" is to be construed broadly as encompassing both ionic and non-ionic species or molecules contained or dissolved in a fluid, including dispersions. The terms "chemical sensors" and "biosensors" are used interchangeably hereinafter.

The microfabrication processes of the invention establish a plurality of thin films and related structures over a planar wafer in a fashion which allows reproducibility and control over the dimensional features of the overlaid structures. In the present invention, such reproducibility and dimensional control have been realized at the wafer level for the mass production of chemical sensors, which sensors incorporate biologically active macromolecules and other reagents necessary for the conversion of selected analyte molecules to more readily detectable species.

This invention also relates to novel electrochemical assay procedures and to novel wholly microfabricated biosensors useful in determining the presence and/or concentration of biological species (analytes) of interest. The invention also relates to a substrate or analyte that does not undergo direct detectable electrochemical oxidation or reduction but which undergoes a reaction with a substrate converter, generally an enzyme, that produces changes in the concentration of electroactive or an optically detectable species. These changes are measured and related proportionately to the concentration of the analyte of interest. Additionally, the invention pertains to methods for making the sensor.

The wholly microfabricated chemical sensor of the present invention comprises multiple elements. The following is a general description of the process for forming the chemical sensor of the invention.

The transducing element is formed on a substantially planar surface, generally a silicon wafer or an optically transparent material. For biosensors based on optical detection the transducing element may be the optically transparent surface onto which other layers are added. Means for supplying excitation wavelengths and adapting optical detectors to such surfaces are well known in the art. For biosensors based on electrochemical detection, e.g. amperometic, potentiometric and conductimetric, means for microfabricating these base sensors or transducing elements onto a planar surface are disclosed in U.S. Pat. No. 5,200, 051, which is incorporated herein by reference in its entirety. Additional structures are then established over the resulting transducing element, which additional structures may include a semipermeable solid film or permselective layer capable of acting as a barrier against interfering chemical species while allowing the transport of smaller detectable chemical moieties of interest. These detectable chemical moieties are typically electroactive molecules and may include low molecular weight ionic species, oxygen, hydrogen peroxide and small redox mediator molecules known in the art. Alternatively, the detectable chemical moieties may be dyes or other optically detectable species generally used in enzyme assays and well known in the art.

The semipermeable solid film may further comprise materials, compounds or molecules that may serve to sensitize the base sensor to a preselected ionic species (e.g., ammonium ion). Most noteworthy are the support matrices described in the instant invention which matrices possess the physical and chemical features necessary to support the various bioactive molecules that constitute the principal means for converting the particular analytes in a given analytical sample into detectable and/or quantitatively measurable species at the transducing element. Techniques are disclosed for localizing or patterning said matrices on certain desired areas of the wholly microfabricated biosensor which allow for the optimum control over dimensional features of the biolayers as well as the versatility to accommodate a wide range of bioactive molecules.

Additionally, the present invention also discloses materials which serve, in particular embodiments of the instant biosensor, as overlaid structures which function as a barrier to the transport of selected analyte species, which are present in high concentrations in the sample. Such analyte barrier (AB) layers allow for a linear sensor response over a wide range of analyte concentrations via the presence of apertures of defined dimensions and positioned at specific locations, which permit a controlled diffusional flux of analyte. Furthermore, the overlaid AB layer, which is preferably derived from a siloxane-nonsiloxane copolymer, is capable of excluding very large molecules or other contaminating constituents of the sample whose direct contact with the underlying structures would result in interference or fouling and an eventual reduction in the reliability of the biosensor. Suitable materials for forming the AB layer are described in U.S. Pat. No. 5,200,051, including the various siloxane-nonsiloxane copolymers set forth therein. In addition to these copolymers, there may be used various polyurethanes, cellulose acetate, tetrafluoroethylene polymers, organic negative photoresists, organic positive photoresists, polyimides and photoformable polyimides.

If the AB layer is of the appropriate structure and composition, it may also function as a gas permeable membrane. In certain embodiments of the present invention, such a gas permeable membrane has the practical advantage of allowing only very small molecules to pass through. These molecules can act as co-reactants in reactions where analyte molecules are converted to species that are detectable at the transducing element.

The AB layer of the instant invention is established on the substrate wafer or any intervening structures with the kind of dimensional, localized, and geometric control which is compatible with other steps in the overall microfabrication process of the instant invention and the notion of an automated, wafer-level mass production of biosensors.

Quite apart from the AB layer mentioned above, a semipermeable solid film which is able to function as a molecular weight-sensitive transmissive film is among the layers which can be established by the methods of the present invention. Depending upon the composition and final thickness of this semipermeable solid film, also referred to as a permselective layer, molecules having molecular weights above a given threshold can be effectively excluded from entering and diffusing through such a film. As a general illustration of the function and utility of this permselective layer, molecules having a molecular weight of about 120 or above are effectively blocked by a solid film having a thickness of about 5 to about 10 nm. Varying degrees of control over the size of the molecules excluded and the rates of transport of smaller molecules which are able to diffuse through the solid film can be obtained with solid films having a thickness in the range of about 2 to about 50 nm. With certain types of materials, these permselective layers may be as thin as 1 nm or may be as thick as 100 nm.

In a preferred embodiment of an amperometric glucose biosensor, a layer of iridium is sputtered onto a silicon wafer and then patterned using established microfabrication processes to form an electrode (diameter 200 $\mu$m) as the transducing element. A permselective layer that permits transport of hydrogen peroxide is then patterned over the iridium electrode according to U.S. Pat. No. 5,212,050, which is incorporated herein by reference in its entirety. A mixture of dichromated photoformable gelatin and the enzyme glucose oxidase is then spin coated onto the wafer and patterned to form a layer of thickness of about 1.0 $\mu$m directly over the electrode, according to the teaching of U.S. Pat. No. 5,200,051. This is followed by patterning a second gelatin diffusion channel (or layer of thickness about 1.0 $\mu$m) that partially covers the enzyme layer and extends beyond the perimeter of the enzyme layer by 50 $\mu$m. A thick AB layer formed from a siloxane-nonsiloxane copolymer is then spin-coated onto the wafer and patterned according to the method disclosed in U.S. Pat. No. 5,200,051 to establish a layer that encloses the first two layers.

Unlike embodiments described in the '051 patent, however, the AB layer thickness (for example, about 1.0 $\mu$m) is sufficient to eliminate detectable glucose permeation directly through this layer. However, the AB layer is still freely permeable to oxygen. A cap layer made from dichromated gelatin is then established in the same way as described in the '051 patent, except that a novel mask design is used to provide for apertures to be formed at specific locations in the AB layer. When the AB layer is etched in the standard manner disclosed in the '051 patent, small apertures (e.g., 5 $\mu$m diameter) are made in the AB layer in the region above the diffusion barrier layer (but not in the region directly above the enzyme layer) through which glucose can pass. Preferably, the size of the aperture(s) is at least about 0.01 $\mu$m by 1.0 $\mu$m (rectangular) or, if circular, having a diameter of from about 0.5 $\mu$m to about 100 $\mu$m. Desirably the diameter is from about 2 $\mu$m to about 10 $\mu$m. Rectangular apertures can be from about 1 $\mu$m to about 20 $\mu$m on the short side and from about 10 $\mu$m to about 3000 $\mu$m on the long side. Desirably, the dimensions of rectangular apertures are from about 3 $\mu$m to about 12 $\mu$m on a short side and from about 50 $\mu$m to about 2000 $\mu$m on a long side. In a preferred embodiment, the rectangular apertures have dimensions of about 5 $\mu$m×1000 $\mu$m.

The apertures may also form an annulus, the thickness of which can vary similar to the diameter dimensions given above.

In certain circumstances it is desirable that a portion of the diffusion layer also contains one or more enzymes that can eliminate specific interferant molecules, e.g. ascorbate and urate. For example the diffusion layer can incorporated ascorbate oxidase or uricase or the like.

The biosensor of the invention may be operated amperometrically in conjunction with a silver-silver chloride reference electrode which is external to the device or incorporated adjacent to the iridium electrode as disclosed in U.S. Pat. No. 5,200,051. Means for activating microfabricated sensors and obtaining reliable data in aqueous and whole-blood samples are disclosed in U.S. Pat. No. 5,112,455 which is incorporated herein by reference in its entirety. Generally, this involves comparing the response of the sensor with a reference electrode in both a calibrant fluid and a sample fluid, relating the signal measurements and then determining the concentration of analyte species in the sample fluid based on the signal relationship. The device described here gives reliable glucose measurements in venous whole blood, which generally has a very low oxygen (co-reactant) concentration (ca. 50 $\mu$m) over the entire range of glucose (analyte molecule) concentrations found in samples from diabetics (ca. 1–30 mM).

With these new devices, it is practical for the aperture(s) to be micron-sized in only one or in both of the x-y dimensions. Thus, for example, an aperture can be a 5 $\mu$m circular pore, a slot of dimensions 5 $\mu$m×1000 $\mu$m, or a ring 5 $\mu$m wide and has a perimeter of 1000 $\mu$m. In addition, the aperture(s) can be positioned directly above the transducing element, or adjacent to the transducing element or formed by patterning the AB layer to leave an exposed edge at the outer perimeter of the diffusion layer.

Another alternative is to make the aperture in the z-x or z-y dimension. This can be achieved by patterning the AB layer to leave an exposed perimeter edge of the second layer. This enables the height (thickness, z-dimension) of the second layer to control one dimension of the aperture while the length of the exposed perimeter controls the other dimension. As the second layer can be spin coated on to a wafer with a controlled thickness in the range 0.01 $\mu$m to 2 mm (which is well known in the microfabrication art), using this method it is possible to fabricate essentially rectangular apertures in the z-x and z-y planes as small as 0.01 $\mu$m z-dimension and 1.0 $\mu$m x-dimension. This provides additional means for controlling the flux of an analyte molecule to the catalyst layer. The particular dimensions of the aperture(s) can be determined by the skilled artisan and are a function of, inter alia, the analyte flux desired and the stoichiometry of the reaction Accurate dimensional control at these geometries is only attainable using microfabrication. Negative and positive organic photoresists, polyurethane, cellulose acetate, polyimide and photoformable polyimide and the like can be used instead of a siloxane-nonsiloxane copolymer to act as co-reactant-permeable, analyte-impermeable AB layers. Where these materials are photoformable, an aperture can be formed directly by exposure and development. Otherwise a patterning method as for the siloxane-nonsiloxane copolymer is required as described above.

In addition to dichromated gelatin and gelatin containing ferric chloride and other photoactivators as described in U.S. Pat. No. 5,200,051, it is also possible to use various other hydrogel materials, for example, a photoformable polyvinyl alcohol material to form both the enzyme layer and the diffusion (or interferant screening) layer. For certain enzymes, e.g. creatinase, the latter enables retention of higher levels of activity.

The general theory applicable to biosensors is well known in the art. For example, U.S. Pat. No. 4,484,987 discloses an equation relating bulk concentrations to those in the enzyme layer. Unlike the '987 patent, embodiments of the present invention include an analyte diffusion layer. If a diffusion coefficient, D, for a typical analyte molecule is $10^{-6}$ cm$^{-2}$s$^{-1}$ in a gelatin or polyvinyl alcohol layer, the diffusion length, I, can be estimated from I=(2Dt)$^{1/2}$, which implies that these molecules can diffuse about 10 $\mu$m in the first second in the plane of the layer. Note that the diffusion coefficient can be controlled by the degree of crosslinking in the layer, e.g. more or less photo-initiator or photo-crosslinker in the matrix, or subsequent treatment with glutaraldehyde or another crosslinker. A method for increasing the porosity and increasing the diffusion coefficient is to add albumin or another globular protein to the matrix before patterning. Thus by changing the length, thickness and composition of the diffusion layer, it is possible to control the response time and the degree the device exhibits an extended linear output response to the analyte molecule even at low co-reactant levels. For example, it has been found that a planar 10–200 $\mu$m diffusion layer between the aperture and the enzyme layer over the transducing element may be used advantageously. It is only by using microfabrication processes, unlike the approaches applied by the prior art, that attaining accurate control and a high level of device to device reproducibility necessary for commercial utility, is possible.

Several embodiments of the invention are shown in the Figures. FIG. 1 illustrates a first embodiment wherein a biosensor is indicated generally by the number 10. A transducing element 12 is placed over a planar surface 14 and an enzyme layer 16 is positioned over the transducing element 12. Surrounding the enzyme layer 16 and the transducing element 12 is a diffusion layer 18 having an edge surface 20. Placed over the enzyme layer 16 and the diffusion layer 18 is an analyte barrier layer 22. A cap 24, used in photoforming apertures in the analyte barrier layer 22, is located over the layer 22. Analyte, such as glucose or creatinine, as well as oxygen, diffuses through the diffusion layer 18 through the edge surface 20. The analyte barrier layer 22, however, permits only oxygen (and other molecules of similar size) to pass through, while preventing larger molecules including analyte, from passing. Thus oxygen diffusion to the enzyme layer 16 occurs over a much larger surface area than does analyte diffusion, thereby compensating for the lower oxygen concentration in a blood sample compared to analyte concentration. Oxygen and analyte are thus at substantially stoichiometric concentration at the enzyme layer 16. The AB layer 22 contains one or more apertures (not shown) which expose the surface of the enzyme layer 15 and/or the diffusion layer 18 to analyte.

Figure 2:
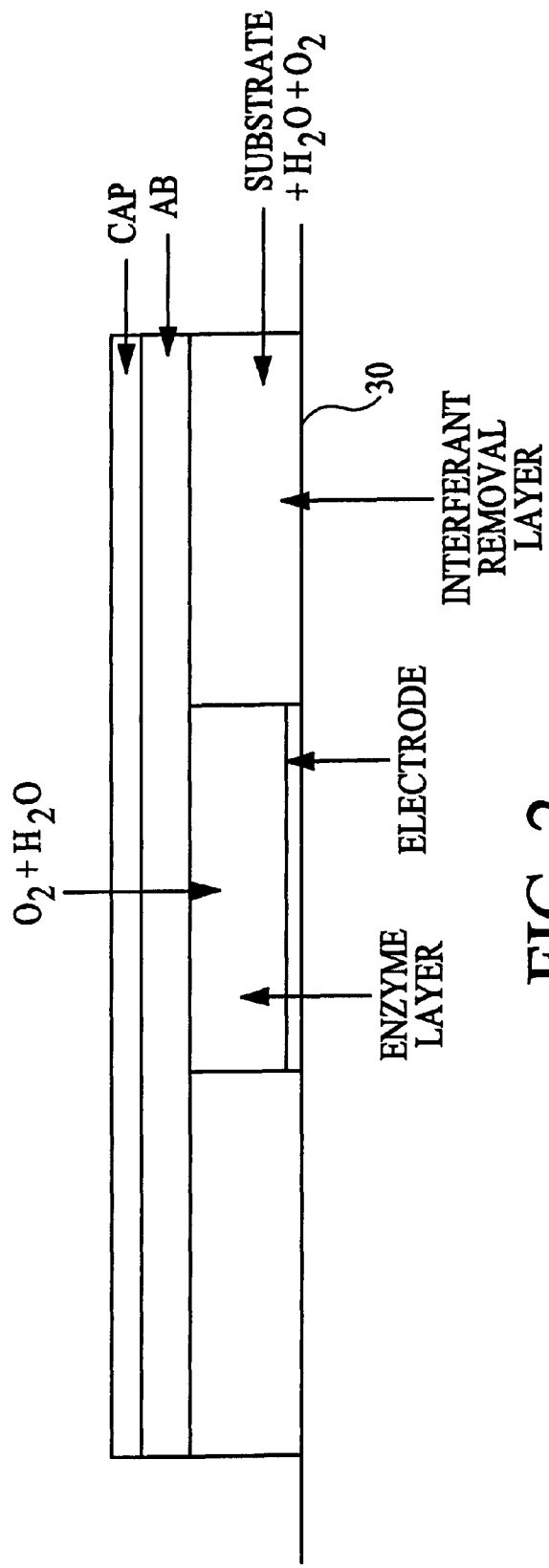
FIG. 2 is a schematic illustrating another embodiment wherein the substrate can only enter the enzyme layer by passing through an edge-plane interferant removal layer, whereas oxygen passes in through the gas permeable layer.
Figure 11:
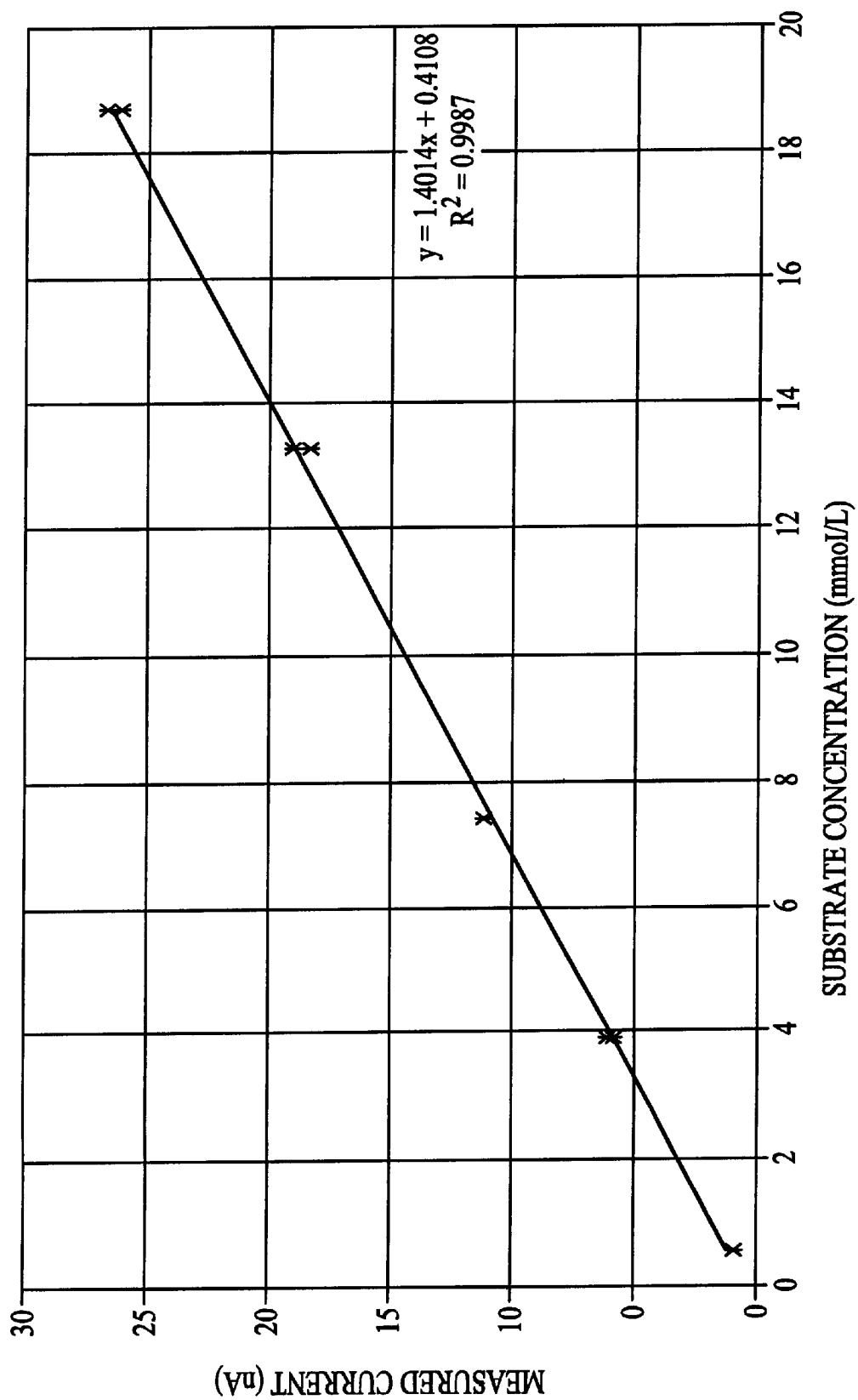
FIG. 11 is a graph showing the response of a lactate sensor of the invention.

A modification of the biosensor of FIG. 1 is illustrated in FIG. 2. In this embodiment the diffusion layer 18 of FIG. 11 is replaced by an interferant removal layer 30 which contains one or more enzymes or catalysts which react with molecules having a potential for interfering with the analysis. The interferant removal layer 30 may be constructed of the same materials as that of the diffusion layer 18, thus providing the dual function of a diffusion layer and interferant removal.

In a preferred embodiment, the various elements of the sensor of FIG. 2 comprise a sensor including a noble metal electrode which functions as an electrocatalyst for $H_2O_2$ electrooxidation; a gamma aminosilane layer which functions to prevent redox-active species that are larger than hydrogen peroxide, e.g. ascorbate and urate, from reaching the electrode surface; an enzyme layer to convert non-electrochemical reactive analyte molecules to hydrogen peroxide; a diffusion layer; and an AB layer from about 0.1–2

μm thick that eliminates analyte molecules such as glucose and creatinine permeating directly into the enzyme layer, but is still freely permeable to oxygen and water. A cap layer is established in the same way as the standard glucose process but the mask provides for apertures to be formed at specific locations. When the AB layer is etched in the standard manner, apertures are made in the AB layer through which analyte molecules can pass. Thus, in this design, the substrate diffusion into the enzyme layer is regulated by the number and size of the apertures in the AB layer and the length of the diffusion path.

Figure 3:
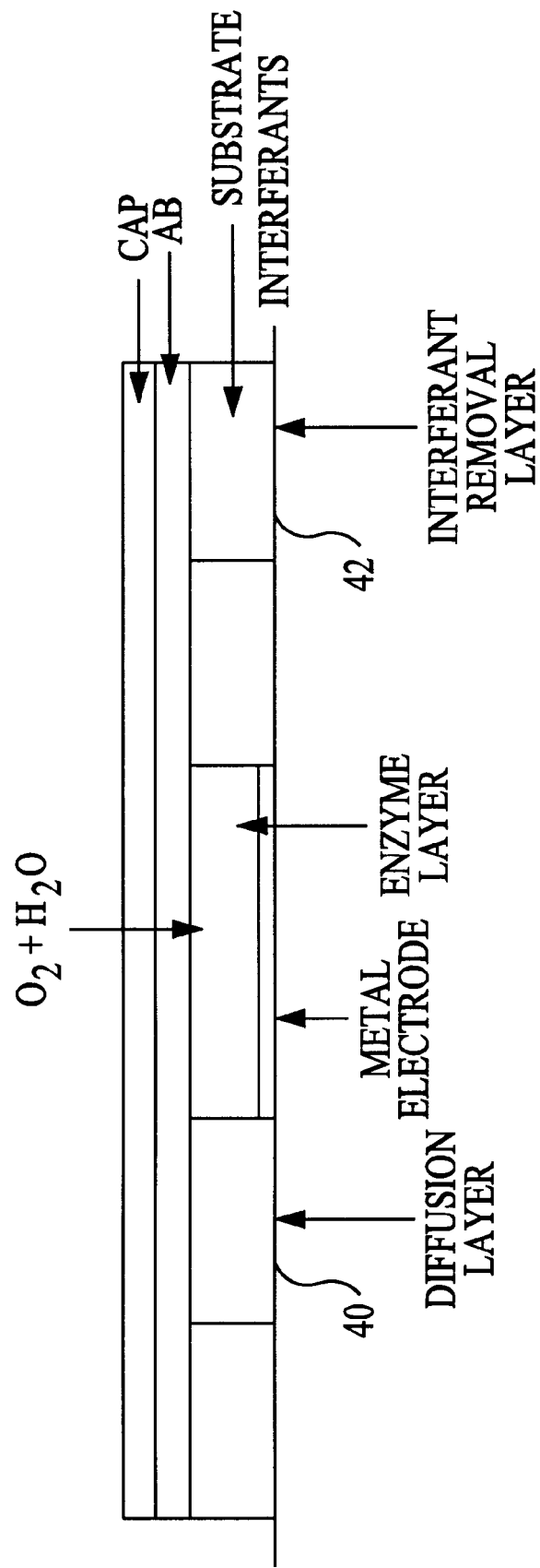
FIG. 3 is a schematic illustrating another embodiment wherein the substrate can only enter the enzyme layer by passing through the edge-plane interferant removal and diffusion layers, whereas oxygen passes in through the gas permeable layer.

FIG. 3 illustrates an embodiment similar to FIGS. 1 and 2 except that it includes both a diffusion layer 40 and an interferant removal layer 42.

Figure 4:
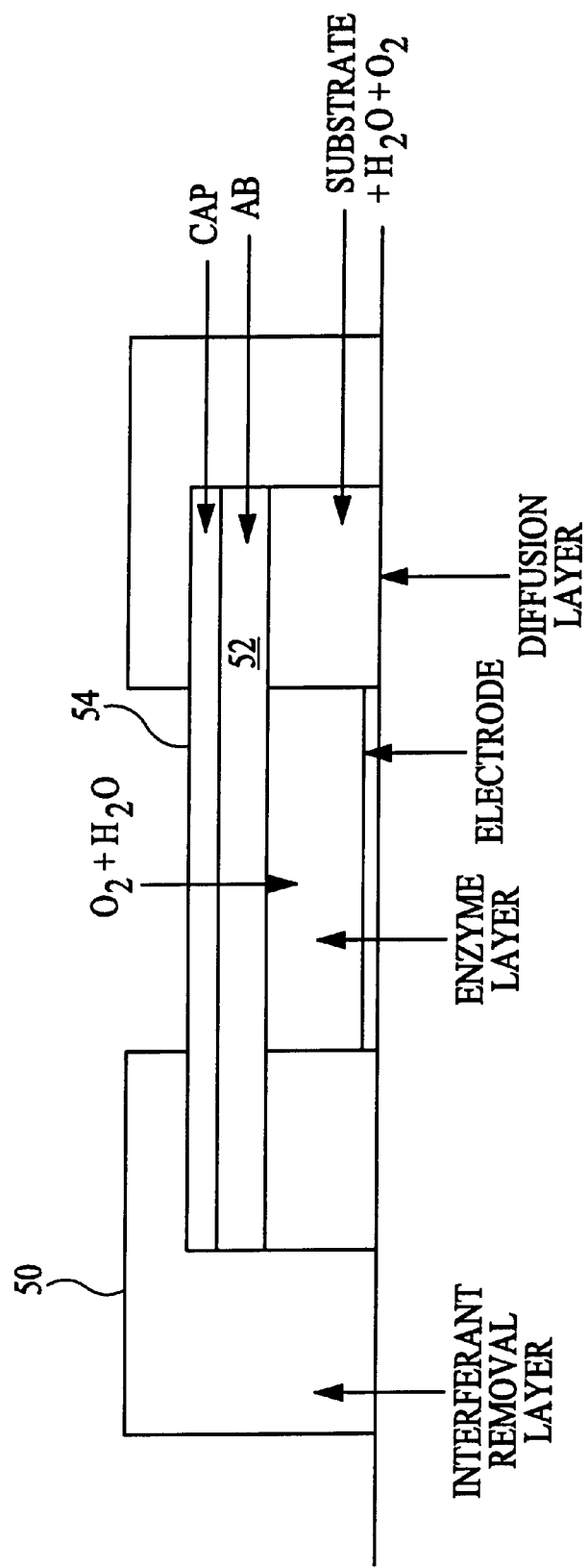
FIG. 4 is a schematic illustrating an embodiment of the invention wherein the substrate can only enter the enzyme layer by passing through the edge-plane interferant removal and diffusion layers, whereas oxygen passes in through the gas permeable layer. In this embodiment the interferant removal layer extends beyond the gas permeable layer.

The embodiment of FIG. 4 is similar to that of FIG. 3 in that it includes separate diffusion and interferant removal layers. However, in this embodiment, the interferant removal layer 50 extends over the edges of the AB layer 52 and cap 54 and covers a portion of the upper surface 56 of cap 54.

Figure 5:
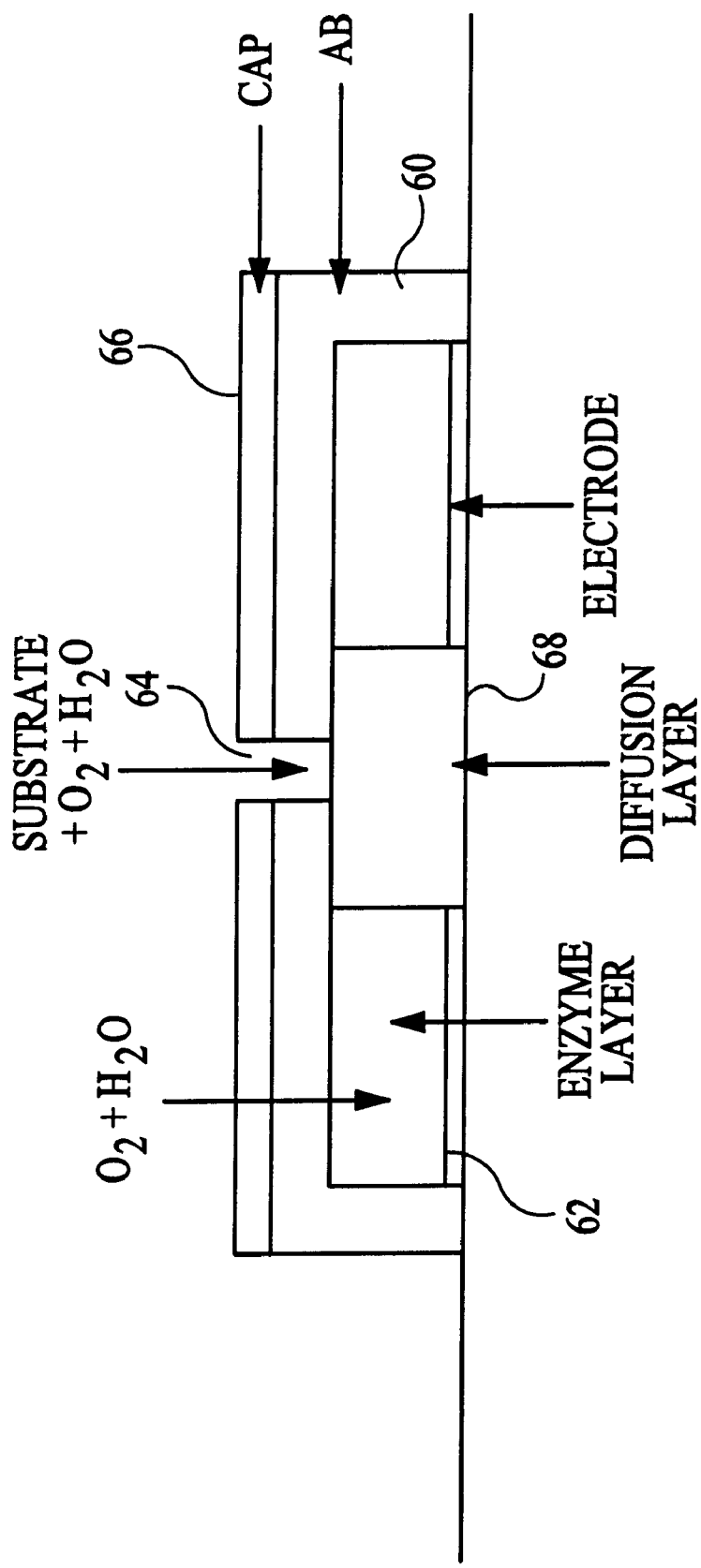
FIG. 5 is a schematic illustrating another embodiment wherein the substrate can only enter the enzyme layer by passing through a pinhole or slot-shaped opening in the gas permeable layer and diffusion layer, whereas oxygen passes in through the gas permeable layer.

In the embodiment of FIG. 5, the AB layer 60 covers the enzyme layer 62. A pinhole 64 is provided through the cap 66 and AB layer 60 to allow substrate to contact the diffusion layer 68. In this embodiment, the electrode 66 and enzyme layer 62 are positioned outward from the diffusion layer 68.

Figure 6:
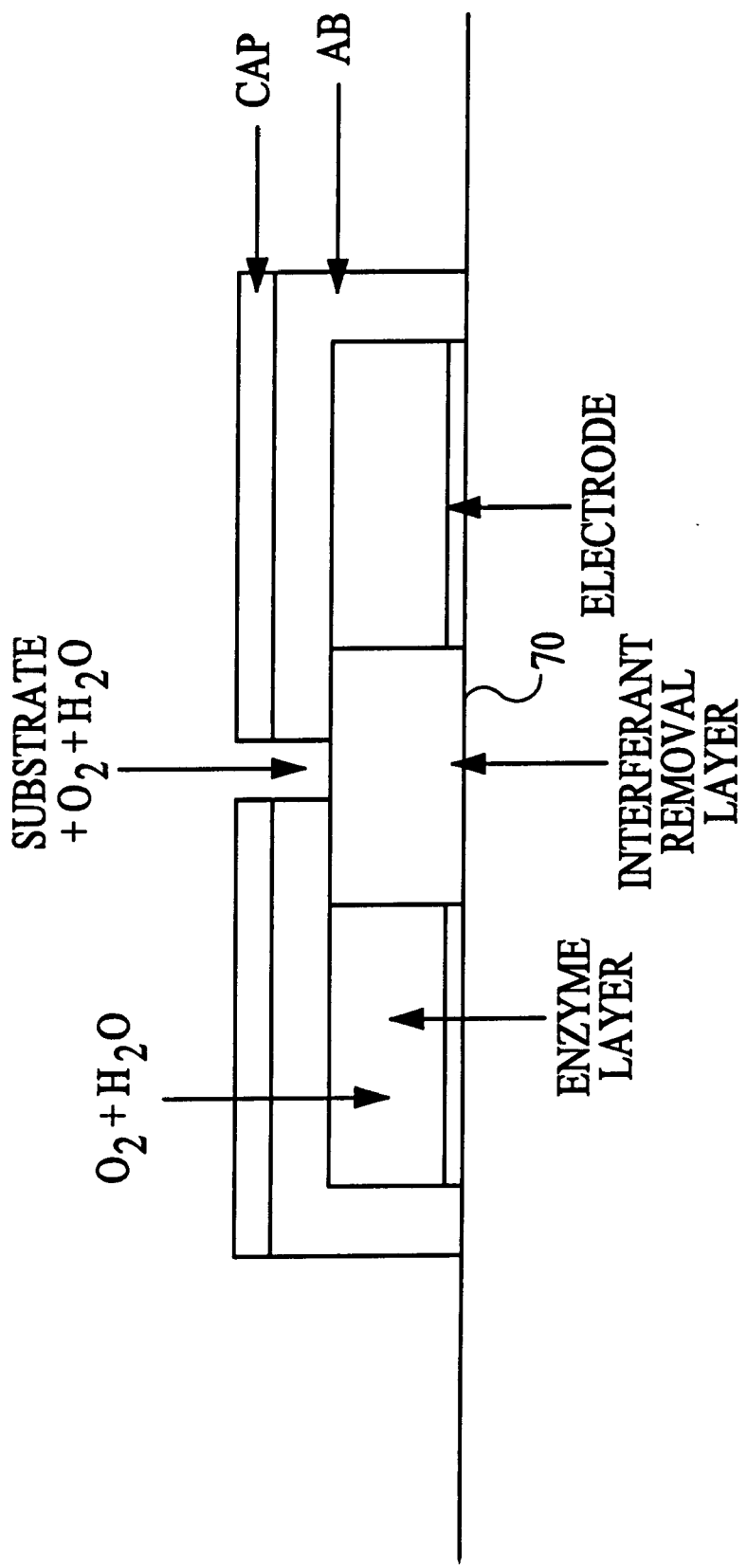
FIG. 6 is a schematic illustrating another embodiment wherein the substrate can only enter the enzyme layer by passing through a pinhole or slot-shaped opening in the gas permeable layer and the interferant removal layer whereas oxygen passes in through the gas permeable layer.

FIG. 6 illustrates an embodiment similar to FIG. 5 except that the diffusion layer is replaced by an interferant removal layer 70.

Figure 7:
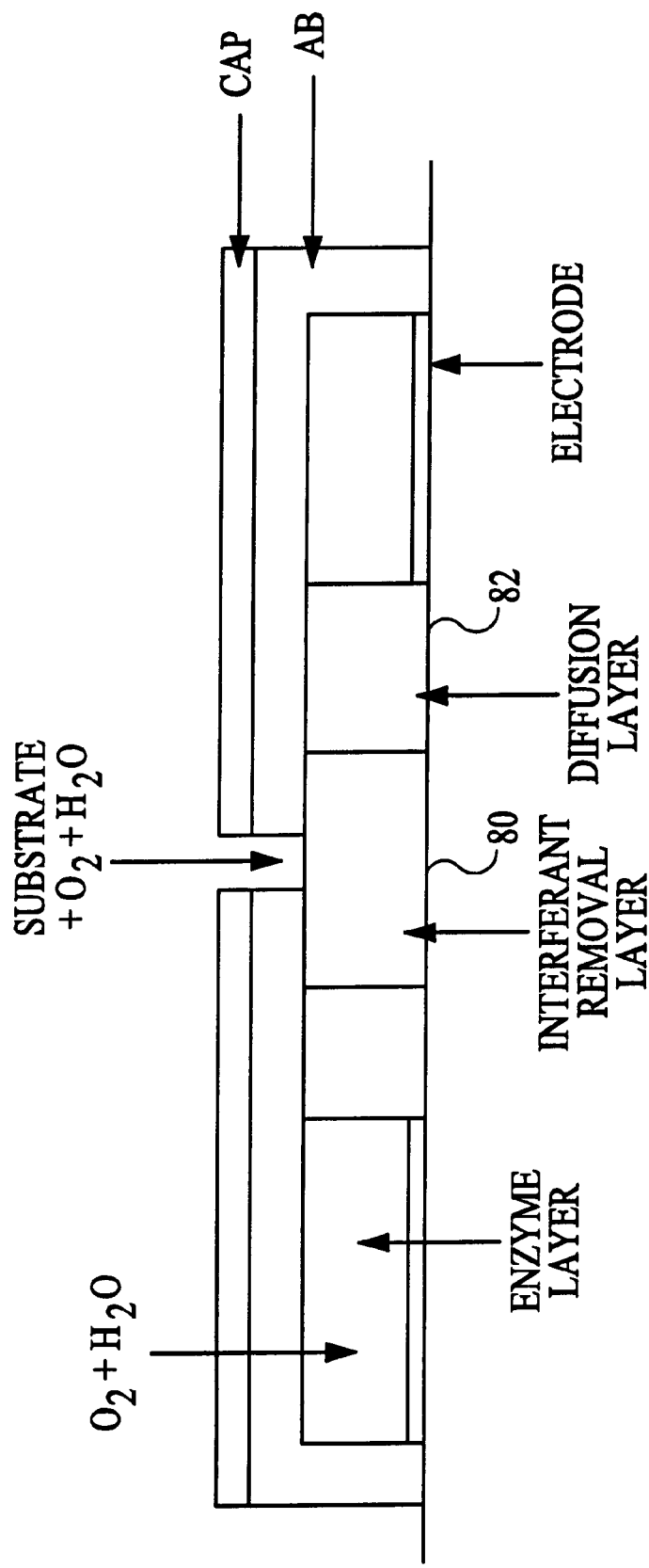
FIG. 7 is a schematic illustrating another embodiment wherein the substrate can only enter the enzyme layer by passing through a pinhole or slot-shaped opening in the gas permeable layer, interferant removal layer and diffusion layer, whereas oxygen passes in through the gas permeable layer.

FIG. 7 illustrates an embodiment configured similar to FIGS. 5 and 6 and incorporating both an interferant removal layer 80 and a diffusion layer 82.

Figure 8:
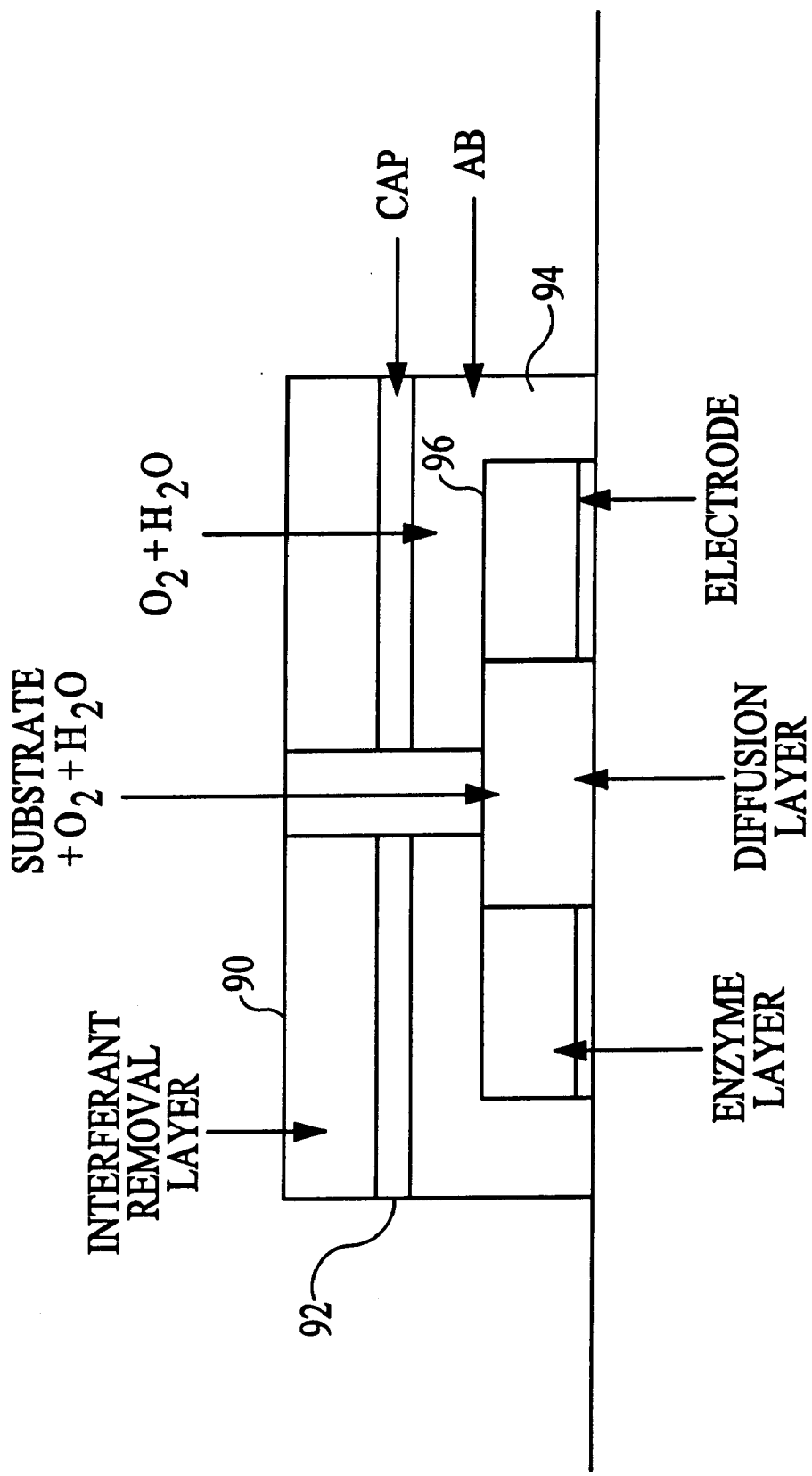
FIG. 8 is a schematic illustrating another embodiment wherein the substrate can only enter the enzyme layer by passing through a pinhole or slot-shaped opening in the gas permeable layer and the diffusion layer, whereas oxygen passes in through the gas permeable layer.
Figure 9:
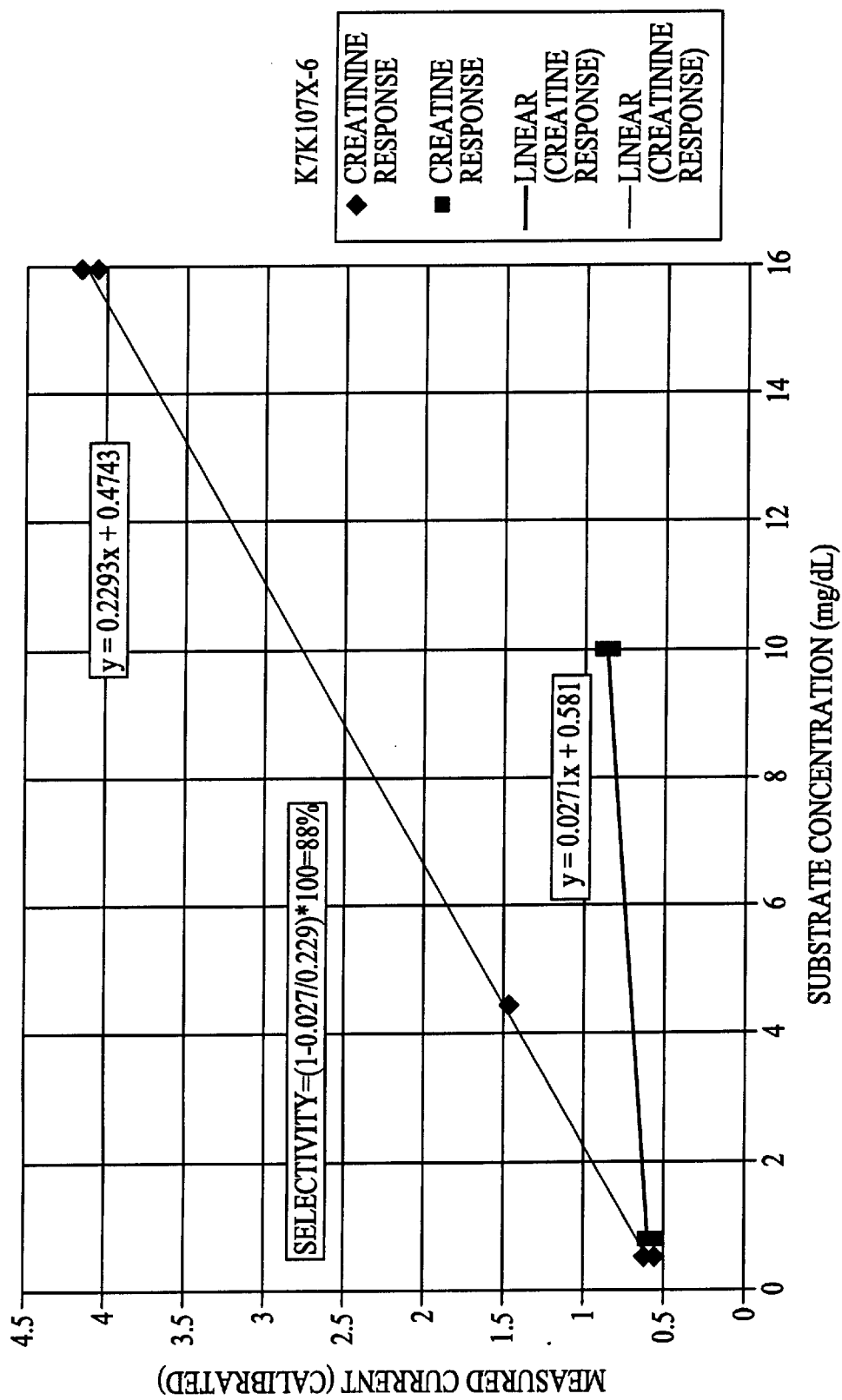
FIG. 9 is a graph showing the response to both creatine and creatinine of the embodiment of FIG. 3, where the interferant screening layer is designed to remove creatine. The response to equimolar creatinine and creatine concentrations over the physiological range is essentially linear and shows that about 90% of the creatine is screened. Note that increasing the length and enzyme loading in the screening layer can improve further upon the screening of creatine, thus increasing the specificity of the device to creatinine.
Figure 10:
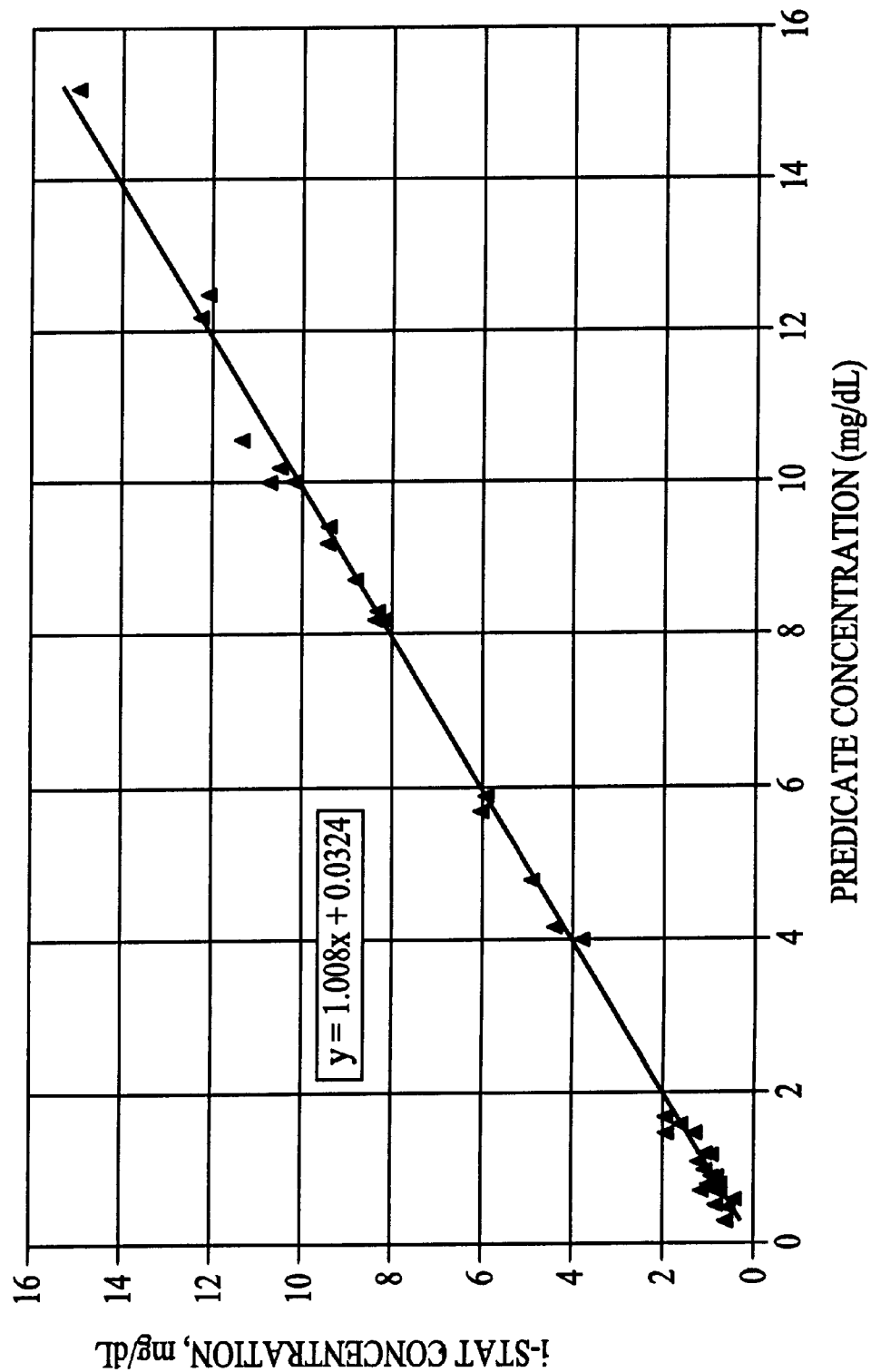
FIG. 10 is a graph showing a comparison for the embodiment of FIG. 3 against a non-microfabricated commercially available creatinine assay on actual blood samples taken from patients. These data show that the new device gives equivalent results and can therefore be used clinically. Data were obtained in accordance with the teaching of U.S. Pat. No. 5,112,455.

FIG. 8 provides for an interferant removal layer 90 positioned over the cap 92 and having an AB layer 94 covering the edge portion of the enzyme layer 96.

The process parameters expand on those disclosed in U.S. Pat. No. 5,200,051. Both platinum and iridium electrodes (diameter 200–360 μm) are used with the standard gamma aminosilane processes in U.S. Pat. No. 5,212,050. Glucose oxidase is immobilized in a dichromated gelatin layer, thickness 0.1–2.0 μm. The standard AB etch time was optimized to ensure no under or over-etch of the aperture, i.e. provide for precise control of aperture diameter.

The determination of creatinine is a good example of an analyte that requires a screening layer to remove interferants. The measurement of creatinine utilizes three enzymes to convert creatinine to hydrogen peroxide. These enzymes are CNH (creatinine a amidohydrolase also called creatininase), CRH (creatine amidinohydrolase also called creatinase) and SAO (sarcosine oxidase) which catalyze the following reactions, respectively.

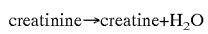

creatinine→creatine+H₂O

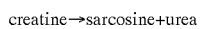

creatine→sarcosine+urea

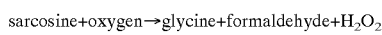

sarcosine+oxygen→glycine+formaldehyde+H₂O₂

The reaction is complicated by the fact that blood naturally contains both creatinine and creatine, thus it is necessary to remove the endogenous creatine before creatinine can be accurately measured. Those skilled in the art will understand that any creatinine that reaches the enzyme layer would produce an erroneous background signal in the determination of creatinine. This problem is solved by creating a creatine-screening layer as part of the creatinine sensor.

For example, the device shown in FIG. 3 is a creatinine sensor that has a diffusion layer and interferant removal layer for creatine. Its function is to prevent the diffusion of the endogenous creatine to the enzyme layer by converting it to non-interfering substances. This layer contains the enzymes CRH, SAO and catalase (CAT). The latter converts hydrogen peroxide to water and oxygen, thus preventing the hydrogen peroxide from diffusing to the transducing element. Note that this combination of enzymes permits the creatinine to diffuse through the screening layer without reaction, and thus reach the enzyme layer.

In this example, enzymes in both layers are immobilized in a photoformable polyvinyl alcohol bearing styrylpyridinium groups (PVA-SbQ). The enzyme layer is confined within the perimeter of the underlying platinum electrode, whereas the diffusion layer and the interferant removal layer extends beyond (20 to 50 μm) the perimeter of the electrode. An AB layer (about 1–2 μm) is then spin-coated over these layers. The thickness of the AB is sufficient to eliminate creatinine (and creatine) permeation into the enzyme layer, but still be freely permeable to oxygen and water. The AB layer is then patterned so that it does not completely enclose the screening layer, thus providing a diffusion path for creatinine (and creatine). The complete creatinine microfabrication process is described in the attached table.

In another embodiment, where reagents other than an enzyme, e.g. ATP, glycerol, a redox mediator molecule, an organic dye molecule, are required in the enzyme or screening layers for reliable sensor operation, these materials may be introduced as part of the enzyme or screening layer matrix deposition process, impregnated after the layers have been established but prior to deposition of the AB layer, adsorbed through the microfabricated apertures after they are formed, or even adsorbed through the apertures as part of the calibration process prior to contacting the sensor with the sample.

The conversion of lactate is catalyzed by the enzyme lactate oxidase and produces hydrogen peroxide, which is detected at a platinum electrode.

Figure 12:
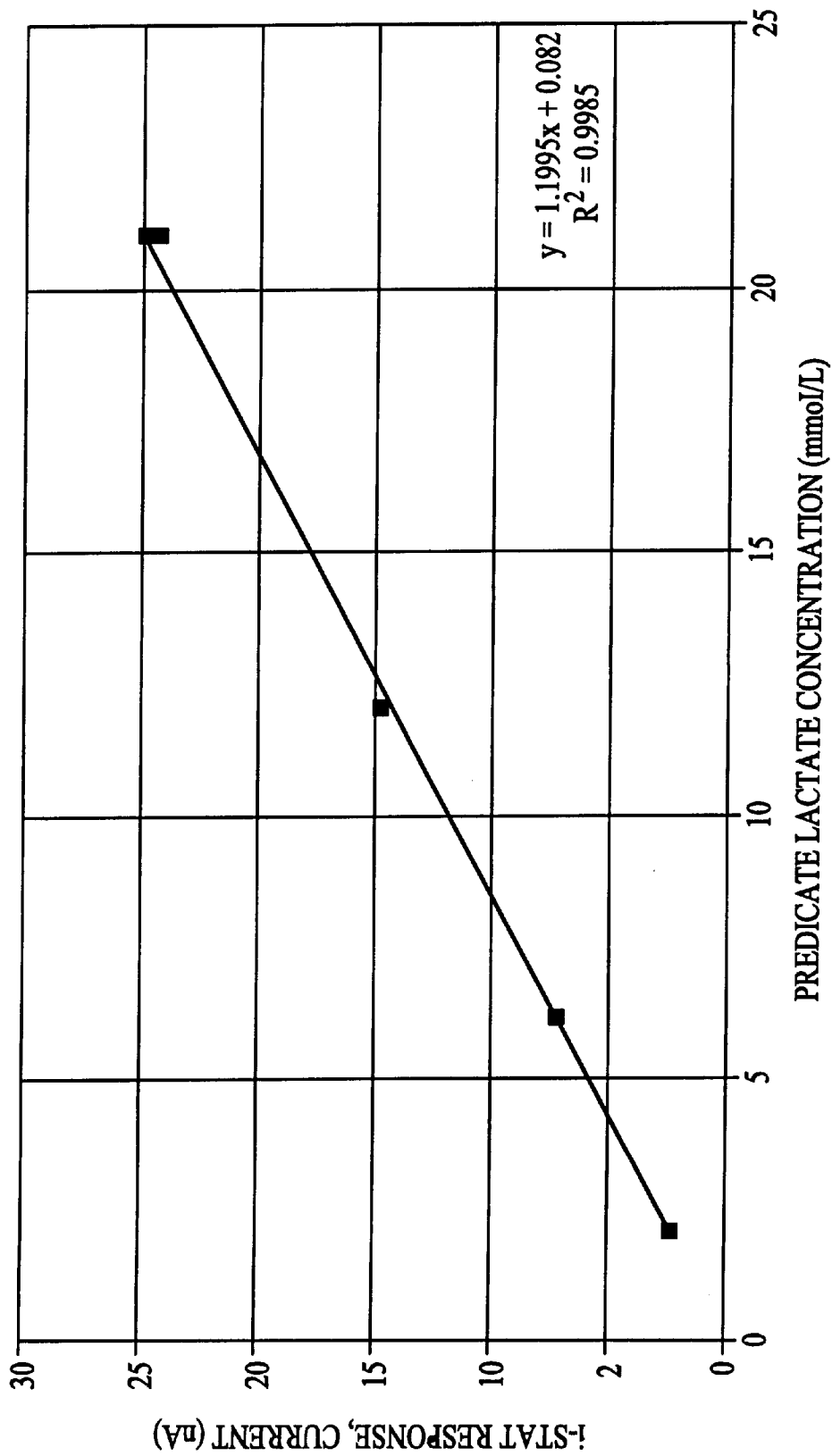
FIG. 12 is a graph of the correlation of the lactate sensor with a lactate assay in whole blood samples.

In a preferred embodiment, the platinum electrode (360 μm diameter) is coated with a gamma aminosilane layer (described above) over which is patterned an enzyme layer (360 μm diameter, polyvinyl alcohol bearing styrylpyridinium groups and lactate oxidase). A diffusion layer (diameter 560 μm, thickness 1.0 μm) is patterned over the enzyme layer and extends beyond its perimeter. A siloxane-nonsiloxane layer is patterned to enclose the entire structure, except for a concentric annular aperture (width 40 μm) which permits lactate to enter the diffusion layer 40 μm beyond the perimeter of the enzyme layer. FIG. 11 shows that the response of the sensor is essentially linear in aqueous samples that correspond to the range of lactate concentrations found in physiological samples. FIG. 12 shows that the sensor provides results that correlate with a commercially established lactate assay in whole-blood samples.

Other related embodiments, based on the disclosure will be apparent to those skilled in the art.

What is claimed is:

1. A microfabricated device for detecting an analyte molecule in a co-reactant-containing sample comprising
 (a) a transducing element;
 (b) a first layer contacting the surface of said transducing element, said first layer comprising a support matrix containing at least one catalyst capable of catalyzing the conversion of said analyte and co-reactant into a reaction product detectable by said transducing element;
 (c) a second layer in contact with said first layer, second layer permitting transport of said analyte molecule and co-reactant; and (d) a third layer covering said first and second layers, said third layer being permeable to co-reactant but substantially impermeable to said analyte molecule and containing at least one microfabricated aperture extending there through, which permits transport of said analyte to said first layer.

2. A microfabricated device as claimed in claim 1, wherein the second layer extends beyond the perimeter of the first layer.

3. A microfabricated device as claimed in claim 1, wherein the at least one aperture in said third layer extends to the first layer.

4. A microfabricated device as claimed in claim 1, where the aperture is in the plane of the third layer.

5. A microfabricated device as claimed in claim 1, where the aperture is in the perimeter of the second layer.

6. A microfabricated device as claimed in claim 5, where the aperture in the second layer is at least about 0.01 $\mu$m by 1.0 $\mu$m.

7. A microfabricated device as claimed in claim 1, wherein the at least one aperture in said third layer extends to a surface of the second layer.

8. A microfabricated device as claimed in claim 7, comprising a plurality of apertures extending to a surface of the second layer.

9. A microfabricated device as claimed in claim 1, comprising a plurality of apertures in said third layer.

10. A microfabricated device as claimed in claim 9, wherein the plurality of apertures are substantially circular.

11. A microfabricated device as claimed in claim 1, wherein the diameter of the aperture is from about 0.5 $\mu$m to about 100 $\mu$m.

12. A microfabricated device as claimed in claim 1, wherein the diameter of said aperture is from about 2 $\mu$m to about 10 $\mu$m.

13. A microfabricated device as claimed in claim 1, wherein the diameter of said aperture is about 5 $\mu$m.

14. A microfabricated device as claimed in claim 1, wherein the aperture is rectangular.

15. A microfabricated device as claimed in claim 14, wherein the aperture has dimensions of from about 1 $\mu$m to about 20 $\mu$m on a short side and from about 10 $\mu$m to about 3000 $\mu$m on a long side.

16. A microfabricated device as claimed in claim 14, wherein the aperture has dimensions of from about 3 $\mu$m to about 12 $\mu$m on a short side and from about 50 $\mu$m to about 2000 $\mu$m on a long side.

17. A microfabricated device as claimed in claim 14, wherein the aperture has dimensions of about 5 $\mu$m on a short side and about 1000 $\mu$m on a long side.

18. A microfabricated device as claimed in claim 1, wherein the plurality of apertures are substantially annular.

19. A microfabricated device as claimed in claim 1, wherein the first layer comprises a photoformable material where the matrix component is selected from the group comprising a proteinaceous material, a gelatin, a hydrogel, a hydrophilic organic polymer and polyvinyl alcohol, and the photoactive material is selected from the group comprising dichromate, ferric chloride a styrylpyridinium salt and a stilbizonium salt.

20. A microfabricated device as claimed in claim 1, wherein the second layer comprises a photoformable material where the matrix component is selected from the group comprising a proteinaceous material, a gelatin, a hydrogel, a hydrophilic organic polymer and polyvinyl alcohol, and the photoactive material is selected from the group comprising dichromate, ferric chloride, a styrylpyridinium salt and a stilbizonium salt.

21. A microfabricated device as claimed in claim 1 wherein the catalyst is an enzyme or combination of enzymes.

22. A microfabricated device as claimed in claim 21, wherein the enzyme or combination of enzymes is selected from the group comprising glucose oxidase, lactate oxidase, pyruvate oxidase, cholesterol oxidase, bilirubin oxidase, sarcosine oxidase, creatinase and creatininase cholesterol esterase.

23. A microfabricated device as claimed in claim 1, wherein the second layer comprises a photoformable gelatin or polyvinyl alcohol layer.

24. A microfabricated device as claimed in claim 1, wherein the third layer is selected from the group comprising a silicone copolymer, polyurethane, cellulose acatate, a siloxane-nonsiloxane copolymer, a tetrafluoroethylene polymer, an organic negative photoresist, an organic positive photoresist, polyimide or a photoformable polyimide.

25. A microfabricated device as claimed in claim 1, wherein the co-reactant is oxygen.

26. A microfabricated device as claimed in claim 1, wherein the analyte molecule is selected from the group comprising glucose, creatine, cholesterol, lactate, pyruvate, sarcosine or bilirubin.

27. A microfabricated device as claimed in claim 1, wherein the first layer has a thickness of from about 0.01 $\mu$m to about 2 mm, the second layer has a thickness of from about 0.01 $\mu$m to about 2 mm, and the third layer has a thickness of from about 0.01 $\mu$m to about 2 mm.

28. A microfabricated device as claimed in claim 1, wherein the catalyst reaction produces an electrochemically detectable reaction product.

29. A microfabricated device as claimed in claim 28, wherein the electrochemically detectable reaction product is selected from the group comprising, oxygen, hydrogen peroxide, a redox mediator, carbon dioxide, hydrogen ion, potassium ion, sodium ion, ammonium ion, calcium ion, fluoride ion.

30. A microfabricated device as claimed in claim 1 wherein the transducer element is an amperometric, potentiometric or conductimetric electrode.

31. A microfabricated device as claimed in claim 1, where the catalyst reaction produces an optically detectable reaction product.

32. A microfabricated device as claimed in claim 1, wherein said transducer element is an optical detector.

33. A microfabricated device as claimed in claim 1, wherein the second layer completely covers, partially covers or abuts the edge of the first layer.

34. A microfabricated device as claimed in claim 1, wherein the second layer incorporates one or more reagent for converting one or more interferant species to non-interferant species.

35. A microfabricated device as claimed in claim 34, wherein one or more reagents are selected from the group ascorbate oxidase, uricase, sarcosine oxidase, creatinase, catalase, biliribin oxidase, lactate oxidase, pyruvate oxidase and glucose oxidase.

36. A microfabricated device as claimed in claim 1, wherein a portion of the second layer that is not in direct contact with the first layer incorporates one or more reagent for converting one or more interferant species to non-interferant species.

37. A microfabricated device as claimed in claim 36, wherein one or more reagents are selected from the group ascorbate oxidase, uricase, sarcosine oxidase, creatinase, catalase, biliribin oxidase, lactate oxidase, pyruvate oxidase and glucose oxidase.

38. A process for manufacturing a planar microfabricated device for detecting an analyte molecule in an oxygen-containing liquid sample comprising:

microfabricating a transducing element on a planar surface;

microfabricating a first layer above said transducing element comprising an enzyme and support matrix, said enzyme capable of converting said analyte and oxygen in a manner detectable at said transducing element;

microfabricating a second layer above said first layer that is permeable to both the analyte molecule and oxygen;

establishing a third layer above said first layer comprising a polymer that is permeable to oxygen, but impermeable to said analyte;

establishing a photoformable layer over said third layer;

exposing said photoformable layer through a mask, said mask containing a pattern for forming one or more apertures of controlled geometry at predetermined locations in said photoformable layer;

developing said pattern;

contacting said photoformed layer with an etchant capable of etching through said third layer to produce a third layer containing one or more microfabricated apertures of controlled geometry at predetermined locations capable of permitting transport of said analyte to said first layer.

39. A process as claimed in claim 38, wherein the first layer comprises a photoformable material where the matrix component is selected from the group comprising a proteinaceous material, a gelatin, a hydrogel, a hydrophilic organic polymer and polyvinyl alcohol, and the photoactive material is selected from the group comprising dichromate, ferric chloride a styrylpyridinium salt and a stilbizonium salt.

40. A process as claimed in claim 38, wherein the second layer comprises a photoformable material where the matrix component is selected from the group comprising a proteinaceous material, a gelatin, a hydrogel, a hydrophilic organic polymer and polyvinyl alcohol, and the photoactive material is selected from the group comprising dichromate, ferric chloride a styrylpyridinium salt and a stilbizonium salt.

41. A process as claimed in claim 38, wherein the enzyme or combination of enzymes is selected from the group comprising glucose oxidase, lactate oxidase, pyruvate oxidase, cholesterol oxidase, bilirubin oxidase, sarcosine oxidase, creatinase and creatininase cholesterol esterase.

42. A microfabricated device as claimed in claim 38, wherein the third layer is selected from the group comprising a silicone copolymer, polyurethane, cellulose acatate, a siloxane-nonsiloxane copolymer, a tetrafluoroethylene polymer, an organic negative photoresist, an organic positive photoresist, polyimide or a photoformable polyimide.

43. A process as claimed in claim 38, wherein the analyte molecule is selected from the group comprising glucose, creatine, cholesterol, lactate, pyruvate, sarcosine or bilirubin.

44. A process for manufacturing a planar microfabricated device for detecting an analyte molecule in an oxygen-containing liquid sample comprising:

microfabricating a transducing element on a planar surface;

microfabricating a first layer above said transducing element comprising an enzyme and support matrix, said enzyme capable of converting said analyte and oxygen in a manner detectable at said transducing element;

microfabricating a second layer above said first layer that is permeable to both the analyte molecule and oxygen;

establishing a third layer which is photoformable above said first layer that is permeable to oxygen, but impermeable to said analyte;

exposing said photoformable layer through a mask, said mask containing a pattern for forming one or more apertures of controlled geometry at predetermined locations;

developing said pattern to produce a third layer containing one or more microfabricated apertures of controlled geometry at predetermined locations capable of permitting transport of said analyte to said first layer.

45. A process as claimed in claim 44, wherein the first layer comprises a photoformable material where the matrix component is selected from the group comprising a proteinaceous material, a gelatin, a hydrogel, a hydrophilic organic polymer and polyvinyl alcohol, and the photoactive material is selected from the group comprising dichromate, ferric chloride a styrylpyridinium salt and a stilbizonium salt.

46. A process as claimed in claim 44, wherein the second layer comprises a photoformable material where the matrix component is selected from the group comprising a proteinaceous material, a gelatin, a hydrogel, a hydrophilic organic polymer and polyvinyl alcohol, and the photoactive material is selected from the group comprising dichromate, ferric chloride a styrylpyridinium salt and a stilbizonium salt.

47. A process as claimed in claim 44, wherein the enzyme or combination of enzymes is selected from the group comprising glucose oxidase, lactate oxidase, pyruvate oxidase, cholesterol oxidase, bilirubin oxidase, sarcosine oxidase, creatinase and creatininase cholesterol esterase.

48. A microfabricated device as claimed in claim 44, wherein the third layer is selected from the group comprising a silicone copolymer, polyurethane, cellulose acatate, a siloxane-nonsiloxane copolymer, a tetrafluoroethylene polymer, an organic negative photoresist, an organic positive photoresist, polyimide or a photoformable polyimide.

49. A process as claimed in claim 44, wherein the analyte molecule is selected from the group comprising glucose, creatine, cholesterol, lactate, pyruvate, sarcosine or bilirubin.

\* \* \* \* \*